(12) United States Patent
Gaillot et al.

(10) Patent No.: US 11,951,036 B2
(45) Date of Patent: Apr. 9, 2024

(54) DROPLET DISPENSING DEVICE AND SYSTEM

(71) Applicant: HOFFMANN-LA ROCHE INC., Little Falls, NJ (US)

(72) Inventors: Maxime Gaillot, Basel (CH); Roberta Leah, Basel (CH); Declan Reilly, Basel (CH); Thomas Thueer, Basel (CH); Jack Carroll, Bristol (GB); James Coop, Bristol Clifton (GB); Edward Sims, Bristol (GB); Mark Teucher, Bath (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 16/760,289

(22) PCT Filed: Nov. 2, 2018

(86) PCT No.: PCT/EP2018/079981
§ 371 (c)(1),
(2) Date: Apr. 29, 2020

(87) PCT Pub. No.: WO2019/086592
PCT Pub. Date: May 9, 2019

(65) Prior Publication Data
US 2021/0401621 A1   Dec. 30, 2021

(30) Foreign Application Priority Data
Nov. 2, 2017  (EP) ..................... 17199765

(51) Int. Cl.
*A61F 9/00*    (2006.01)
(52) U.S. Cl.
CPC ................. *A61F 9/0008* (2013.01)

(58) Field of Classification Search
CPC ......... A61F 9/0008; A61M 5/00; B05B 11/06
See application file for complete search history.

(56) References Cited

U.S. PATENT DOCUMENTS 2,589,178 A * 3/1952 Wintle, Jr. ............ A61F 9/0008
                                                            604/298
4,588,403 A * 5/1986 Weiss .................... A61M 5/162
                                                            604/414

(Continued)

FOREIGN PATENT DOCUMENTS

| CN | 1802143 A | 7/2006 |
| CN | 101588780 A | 11/2009 |

(Continued)

OTHER PUBLICATIONS

International Search Report dated Jan. 29, 2019 in PCT/EP2018/079981.

(Continued)

*Primary Examiner* — Benjamin J Klein
*Assistant Examiner* — Hans Kaliher
(74) *Attorney, Agent, or Firm* — MEDLER FERRO WOODHOUSE & MILLS PLLC

(57) ABSTRACT

A device for providing a droplet of a liquid stored in an interior of a vial is disclosed that includes a support body and a resilient dome portion mounted to the support body to form a chamber having air, with the dome portion being configured to create an air flow when activated by compression. The support body includes a vial seat, a nozzle, and air flow and transfer conduits. The support body is arranged, when the vial is received by the vial seat, such that the air flow conduit establishes an air connection between the vial interior and the chamber, the transfer conduit establishes a fluid connection between the vial and the nozzle, and, upon activation of the dome portion, the air flow delivers air into (Continued)

Figure 1:
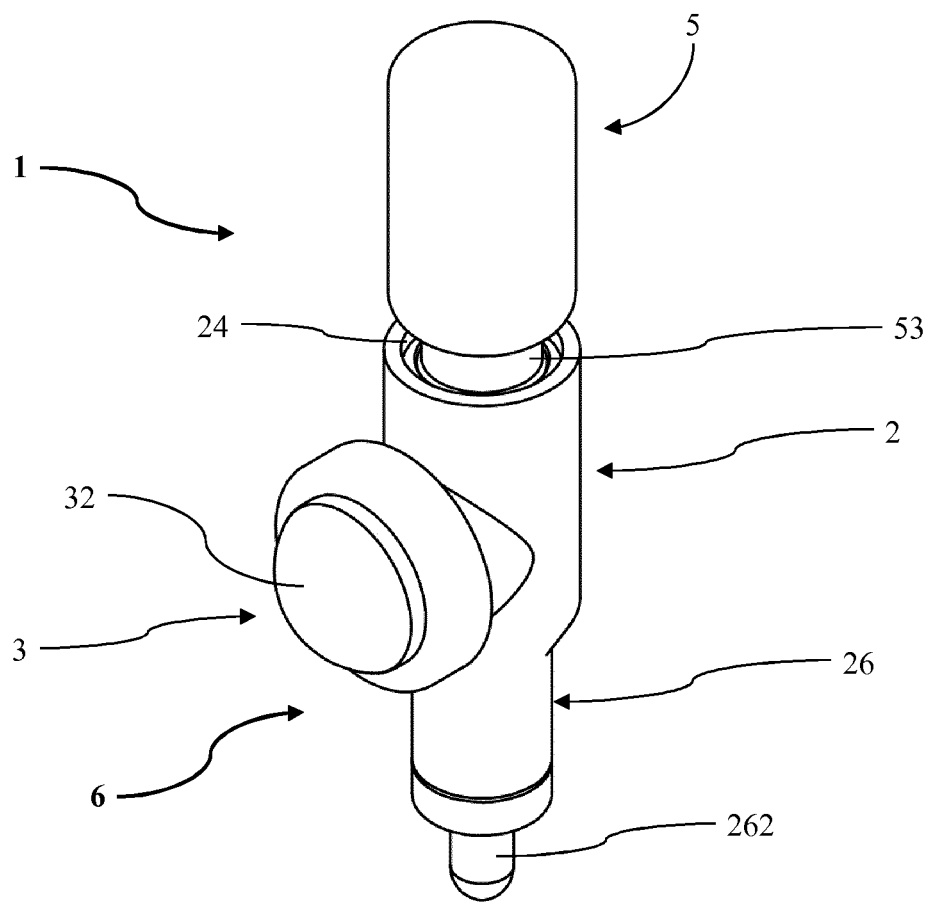

the vial that causes liquid to be transferred from the vial to the nozzle through the transfer conduit.

17 Claims, 2 Drawing Sheets

(56) References Cited

U.S. PATENT DOCUMENTS

| | | | |
|---|---|---|---|
| 6,948,522 B2 | 9/2005 | Newbrough et al. | |
| 7,900,659 B2 | 3/2011 | Whitley et al. | |
| 8,172,115 B1* | 5/2012 | Mulhauser | B05B 11/061 |
| | | | 239/338 |
| 8,333,193 B2* | 12/2012 | Yamashita | A61P 11/00 |
| | | | 128/203.23 |
| 9,402,765 B2* | 8/2016 | Chibret | B65D 47/18 |
| 2006/0081726 A1* | 4/2006 | Gerondale | A61F 9/0008 |
| | | | 239/590 |
| 2007/0051362 A1* | 3/2007 | Sullivan | A61M 15/0038 |
| | | | 128/200.23 |
| 2007/0102455 A1* | 5/2007 | Stark | B05B 11/1032 |
| | | | 222/207 |
| 2007/0145076 A1* | 6/2007 | Yamada | A61F 9/0008 |
| | | | 222/189.09 |
| 2011/0175347 A1 | 7/2011 | Okiyama | |
| 2012/0197184 A1 | 8/2012 | Okuda et al. | |
| 2014/0238532 A1* | 8/2014 | Fangrow | A61J 1/2072 |
| | | | 141/2 |
| 2017/0095404 A1 | 4/2017 | Fangrow | |

FOREIGN PATENT DOCUMENTS

| | | |
|---|---|---|
| CN | 102196798 A | 9/2011 |
| CN | 102497846 A | 6/2012 |
| EP | 1 402 913 A1 | 3/2004 |
| EP | 1 779 933 A1 | 5/2007 |
| JP | S64-42044 U | 3/1989 |
| JP | 2008024339 A | 2/2008 |
| JP | 2010168119 A | 8/2010 |
| WO | 2011126569 A1 | 10/2011 |
| WO | 2014116602 A1 | 7/2014 |

OTHER PUBLICATIONS

Office Action issued Jan. 21, 2022 in Chinese Patent Appln. No. 201880069916.9.

Japanese Office Action dated Sep. 1, 2022 issued in corresponding Japanese Patent Application No. 2020-523975.

* cited by examiner

DROPLET DISPENSING DEVICE AND SYSTEM

TECHNICAL FIELD

The present invention relates to a droplet dispensing device and a respective system for providing droplets of liquids. Such devices and systems are, e.g. used in therapeutic or caregiving applications where droplets of medicaments or other liquids are to be administered.

BACKGROUND ART

In many therapeutic treatments, pharmaceutical products (below referred to as drug products) are processed and/or administered in droplets, e.g. into body openings or on locations of the body to be treated. For example, in ophthalmologic applications drugs are often administered in droplets directly into the eye. For this purpose, it is known to use devices like pre-filled eye dropper bottles, blow-fill-seal devices or similar specific droplet dispensers.

However, such devices typically require a significant investment and cause a comparably large effort in production. Therefore, they are usually not appropriate for clinical studies and the like. In such applications, if administered in liquid form, the drug products usually are provided in specific containers such as in vials, bottles or the like. For delivering the drug products, they are withdrawn from the containers into a transfer syringe or a similar device and dispensed into a container that can dispense droplets.

Using such transfer syringes or similar devices, however, typically involves a comparably large number of handling steps which increases the risk of use errors. Also, it is comparably inconvenient for a person preparing the drug product for administration.

Therefore, there is a need for a device or system allowing a comparably safe and efficient delivery of a liquid drug product in the form of droplets.

DISCLOSURE OF THE INVENTION

According to the invention this need is settled by a device as it is defined by the features of independent claim 1, and by a system as it is defined by the features of independent claim 14. Preferred embodiments are subject of the dependent claims.

In particular, the invention deals with a device for providing a droplet of a liquid stored in an interior of a vial.

The term "vial" as used herein can relate to a vial in the literal sense, i.e. a comparably small vessel or bottle, often used to store pharmaceutical products or drug products in liquid, powdered or capsuled form. The vial can be made of a sterilizable material such as glass or plastic such as, e.g., polypropylene. It typically comprises a cover or cap including a sealing such as a rubber stopper or a septum which for many applications is designed to be pierced.

The term "drug" can relate to a therapeutically active substance, also commonly called active pharmaceutical ingredient (API), as well as to a plurality of such therapeutically active substances. The term also encompasses diagnostic or imaging agents, like for example contrast agents (e.g. MRI contrast agents), tracers (e.g. PET tracers) and hormones, that need to be administered in liquid form to the patient.

The term "drug product" as used herein relates to a drug as defined above formulated or reconstituted in a form that is suitable for administration to the patient. A particularly preferred drug product can be a drug solution, in particular a solution for body opening administration, injection or infusion. The liquid in the vial can particularly be such a drug product.

The term "droplet" or drop as used herein relates to a comparably small column or volume of liquid. Typically, droplets are bounded completely or almost completely by free surfaces. A droplet may form when liquid accumulates at an end of a tube or other tubular structure.

The device according to the invention comprises a support body and a resilient dome portion. The dome portion is mounted to the support body to form a chamber comprising air. In a certain embodiment the dome portion is tightly mounted to the support body so that it is air tight. In another embodiment the dome portion is not tightly mounted to the support body so that it is not air tight. It is configured to create an air flow with the air in the chamber when activated by compression and re-expansion.

The term "activation" as used herein can relate to bringing the dome portion in a deformed shape and to bringing the dome back in its original shape. For example, bringing the dome portion in a deformed shape, i.e. deforming the dome portion, can be achieved by compressing or pushing it, such as compressing it with a finger. Bringing the dome portion back in its original shape can be achieved, for example, by releasing the dome portion such that resiliency or elasticity of the material of the dome portion re-expands it to the original shape.

The support body of the device according to the invention comprises a vial seat arranged to receive the vial, a nozzle, an air flow conduit and a transfer conduit connecting the vial seat with the nozzle. The vial seat can be configured to engage and hold the vial in a predefined position. It can allow for a seal arrangement of the vial such that the liquid can be tightly transferred. The conduits may be embodied as channels, ducts or bores in the support body.

The support body is arranged that, when the vial is received by or in the vial seat, (i) the air flow conduit establishes a fluid connection between the interior of the vial and the chamber, (ii) the transfer conduit establishes a fluid connection between the vial and the nozzle, and (iii) on activation of the dome portion, the air flow delivers air into the vial such that a pressure rise is created in the interior of the vial which causes liquid to be transferred from the vial to the nozzle through the transfer conduit.

The term "fluid" as used herein relates to a substance that more or less continually deforms, i.e. flows, under an applied shear stress. A fluid may be a liquid such as the drug product, a gas such as air, a plasma and, to some extent, solids compositions. In the context of the invention, the term fluid is typically used in connection with the liquid drug product and the air or other gas inside the chamber and the vial.

In operation of the device according to the invention, the vial with the liquid in its interior is mounted to the vial seat. Thereby, the transfer conduit and the air flow conduit access the interior of the vial. Preferably, when the vial is received by the vial seat, compression of the activation of the dome portion causes air to be delivered into the interior of the vial. In particular, by compressing the dome portion within activation, the air flow is generated such that air is transferred from the chamber into the interior of the vial. Thereby, the pressure inside the vial is increased and liquid is forwarded from the vial to the nozzle. From the nozzle the liquid is provided in droplets or eventually a specific jet and administered as desired.

The device according to the invention provides a comparably simple and safe mechanism to actively deliver droplets such as eye drops directly from the vial. Like this, the number of handling steps can be significantly reduced. In particular, it can be reduced to inserting or mounting the vial and activating the dome portion. Furthermore, the device can be intuitive to use such that the danger of misuse can be reduced and safety in application can be increased. Also, the closed transfer conduit and nozzle volumes can enable a comparably accurate dosing. In particular, the dome portion or the chamber are part of the closed volume such that a continuous or following flow of the liquid after activation of the dome portion can be prevented.

Still further, the device according to the invention can be manufactured in a comparably cost efficient manner. For example, standard manufacturing technology such as injection molding can be used for manufacture. Also, the device can be composed of comparably few parts or pieces. For example, it can be composed of two or more parts, i.e., the dome portion of a comparably resilient or elastic deformable material and the support portion of a comparably rigid material. Preferably, the dome portion is made of silicone or of some similar compliant, flexible elastomeric material. It may be a moulded silicone part which can easily come back to its original moulded shape after deformation by compression. The support body made of a more rigid material than the dome portion to better support the deformable dome portion can be injection moulded of a thermoplastic polymer.

Thus, the device according to the invention can be particularly suitable for clinical studies or trials.

Preferably, the air flow conduit comprises an end section embodied as puncturing member protruding the vial seat and arranged to pierce a cover of the vial to establish a flow pathway between the chamber and the interior of the vial. The puncturing member can particularly be embodied as a spike or a needle section. Such puncturing member allows for assuring an efficient and safe access to the interior of the vial when the latter is mounted to or received by the vial seat.

Additionally or alternatively, the transfer conduit preferably comprises an end section embodied as puncturing member protruding the vial seat and arranged to pierce a cover of the vial to establish a flow pathway between the nozzle and the interior of the vial. Also this puncturing member can particularly be embodied as a spike or a needle section. The puncturing member of the air flow conduit and the puncturing member of the transfer conduit can be one single piece or part. They can particularly be integrated in the same single spike arrangement. Such puncturing member allows for assuring an efficient and safe access to the interior of the vial when the latter is mounted to or received by the vial seat.

Thereby, the puncturing member of the air flow conduit preferably protrudes the puncturing member of the transfer conduit. Since the transfer conduit is intended to transfer the liquid from the vial, it advantageously ends close to the cover of the vial such that essentially all liquid in the vial can be accessed. In contrast, for the air flow conduit, it can be beneficial to extend further into the interior of the vial for efficiently forwarding the air into it.

In this context, the puncturing member of the transfer conduit preferably is dimensioned to end in, or adjacent to, the cover of the vial, when the vial is received by the vial seat. The puncturing member of the air flow conduit preferably is dimensioned to end outside the liquid in the interior of the vial, when the vial is received by the vial seat. Like this, it can be prevented that air is provided through the liquid inside the vial which may cause bubbles and turbulence in the liquid inside the vial. Also, it may be achieved that no liquid is withdrawn from the vial into the chamber upon re-expansion of the dome portion.

Preferably, the device is configured so that, when the vial is received by the vial seat, compression of the activation of the dome portion causes air to be delivered into the interior of the vial. With the actively performed compression, air can be pushed into the vial such that the pressure in the interior of the vial can sufficiently be raised to forward the drug product through the transfer conduit.

Preferably, the device is configured so that, when the vial is received by the vial seat, re-expansion of the activation of the dome portion causes air to be drawn through the nozzle into the interior of the vial and to the chamber. Like this, the pressure inside the vial can efficiently be equalized.

Preferably, the device comprises an air permeable and liquid tight filter member separating the chamber from the air flow conduit. The filter member can be arranged as a sidewall of the air flow conduit separating the latter from the chamber. It can also be positioned anywhere else in the air flow conduit and, advantageously, close to the end section thereof. By means of such filter member, it can efficiently be prevented that liquid of the vial enters into the chamber.

Preferably, the device comprises an air duct arranged to create an air flow pathway from the transfer conduit to an exterior of the device. With such an air duct it may be achieved that the air for pressure equalization inside the vial has not to be withdrawn through the nozzle. This may increase efficiency of the device and, particularly, prevent that air is supplied in the beginning of an activation step.

Thereby, the device preferably comprises a one-way valve arranged to prevent liquid to be delivered from the transfer conduit through the air duct.

Preferably, the nozzle of the support body comprises a socket and an exchangeable nozzle insert. Such a nozzle allows for adjusting the droplet provision to an intended application. For example, by selecting an appropriate nozzle insert the droplet size may be adapted such that the dose of the liquid or drug product is adjusted. Thereby, the nozzle of the support body comprises a seal positioned between the socket and the nozzle insert. Like this, the nozzle insert can be efficiently connected to the socket in a seal manner.

Preferably, the nozzle comprises a droplet duct with an open end, the droplet duct extending between the transfer conduit and the open end, and having a droplet generation section of reduced diameter. With such a droplet duct, the size and shape of the droplets provided can efficiently be adapted.

Another aspect of the present invention relates to a droplet dispensing system comprising a device as described above and a vial with an interior in which a liquid to be dispensed is arranged. Such a system allows for efficiently achieving the effects and benefits described above in connection with the device according to the invention and its preferred embodiments.

BRIEF DESCRIPTION OF THE DRAWINGS

The device and the system according to the invention are described in more detail herein below by way of exemplary embodiments and with reference to the attached drawings, in which:

FIG. 1 shows a perspective view of a system according to the invention comprising a first embodiment of a device according to the invention;

FIG. 2 shows a cross sectional view of the system of FIG. 1; and FIG. 3 shows cross sectional view of a system according to the invention comprising a second embodiment of a device according to the invention.

DESCRIPTION OF EMBODIMENTS

In the following description certain terms might be used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to in previous or following description sections. Further, for reason of lucidity, if in a drawing not all features of a part are provided with reference signs it is referred to other drawings showing the same part. Like numbers in two or more figures represent the same or similar elements.

Figure 2:
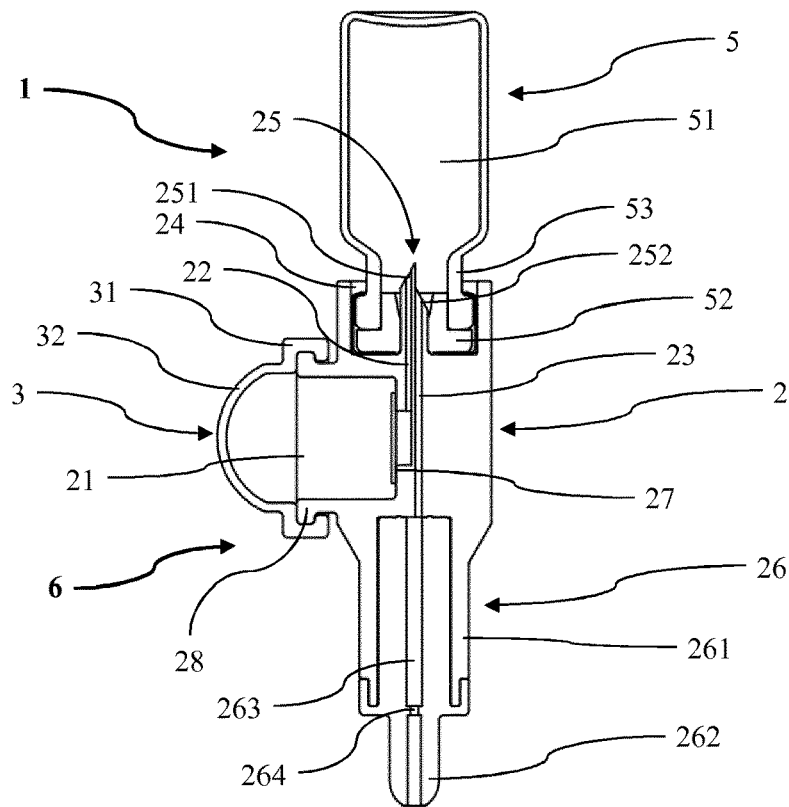
Figure 3:
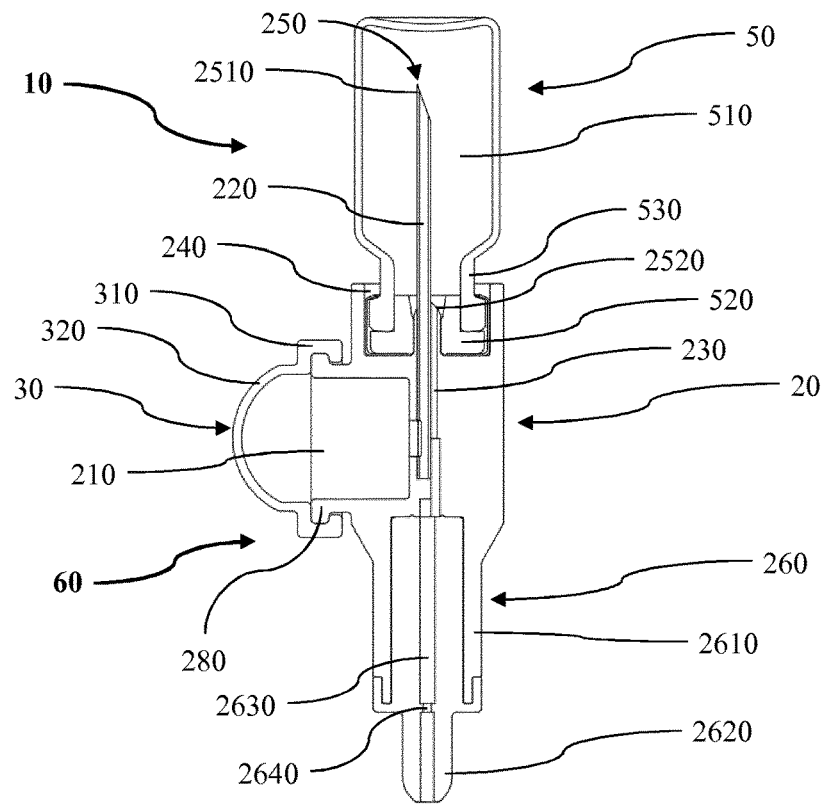

In FIG. 1 and FIG. 2 a system 1 according to the invention is shown comprising a first embodiment of a device 6 according to the invention and a vial 5 with a liquid ophthalmic drug product intended to be administered dropwise into the eye of a patient. The vial 5 is a common bottle-like vial 5 having a hollow interior 51 in which the drug product is arranged, a neck 53 with an opening closed by a cover 52. The cover 52 includes a septum sealing the opening of the neck 53 and a cap holding the septum.

The device 6 comprises a rigid support body 2 and an elastic spherical dome 3 as dome portion with an actuation portion 32. In other embodiments the dome can also be non-spherical such as for example a flat surface. The body 2 is equipped with a ring shaped mounting flange 28 and the dome 3 with a corresponding mounting notch 31. The dome 3 is put on the body 2 such that the mounting flange 28 is arranged inside the mounting notch 31 thereby forming a tight connection between the dome 3 and the body 2. The dome 3 together with the body 2 forms a chamber 21 filled with air.

At its upper end, the body 2 comprises a vial seat 24 and, at its bottom end, a nozzle 26. Between the chamber 21 and the vial seat 24 a straight air flow conduit 22 extends. Similarly, between the nozzle 26 and the vial seat 24 a straight transfer conduit 23 extends. In a certain embodiment, a top air flow conduit end section 251 of the air flow conduit 22 projects above or protrudes a top transfer conduit end section 252 of the transfer conduit 23. In another embodiment, the top air flow conduit end section 251 of the air flow conduit 22 can also be level or beneath a top transfer conduit end section 252 of the transfer conduit 23. The air flow conduit end section 251 and the transfer conduit end section 252 together form a spike 25 as puncturing member.

As can be best seen in FIG. 2, the body 2 is embodied such that the spike 25 pierces the septum of the cover 52 when the vial 5 is received by the vial seat 24. More particularly, for mounting the vial 5 to the body 2 it is pushed upside down, i.e. head first, into the vial seat 24. Thereby, the spike 25 is pressed through the cover 52. The vial 5 is then safely held in the vial seat 24.

The spike 25 is shaped and dimensioned such that the transfer conduit 23 ends in the cover 52 of the vial 5. Thereby, the transfer conduit end section 252 is positioned at or close to the top end of cover 52. The spike 25 further is shaped and dimensioned such that the air flow conduit 22 projects above the transfer conduit end section 252. Thereby, the air flow conduit end section 251 is positioned in the interior 51 of the vial 5.

The nozzle 26 of the body 2 comprises a socket 261 and an insert 262 with a straight nozzle duct 263. In particular, the insert 262 is forwarded bottom up into the socket 261 and fixed thereto, e.g., by a snap feature or bayonet closure. Thereby, the nozzle duct 263 is in line and in fluid connection with transfer conduit 23. The socket 261 and the insert 262 are sealed to each other by means of an O-ring or moulded gasket positioned in between (not visible in the Figs.). The nozzle duct 263 is equipped with a neck 264 which has a reduced diameter compared to the rest of the nozzle duct 263.

The transfer conduit 23 establishes a fluid pathway between the interior 51 of the vial 5 and the nozzle 26. The air flow conduit 22 establishes a fluid pathway between the interior 51 of the vial 5 and the chamber 21. A liquid tight but air permeable filter 27 is arranged as wall member between the chamber 21 and the air flow conduit 22.

In operation of the system 1, the dome 3 is activated by compressing and releasing the actuation portion 32 with a finger of a user operating the system 1. In particular, when compressing the dome 3 air of the chamber 21 is pushed through the filter 27 into the air flow conduit 22 such that an air flow is generated from the chamber 21 to the interior 51 of the vial 5. Like this, a pressure in the interior 51 is raised and the drug product is forwarded into the transfer conduit 23 such that a liquid flow is generated from the interior 51 of the vial 5 to the nozzle 26. In the nozzle 26, the liquid is formed to droplets by the droplet forming section or insert 262. In particular, the shape and dimension of the insert 262 define the shape and dimension of the droplets provided by the system. Thus, by selecting an appropriate insert 262, the system 1 can be adapted to allow provision of droplets of the drug product as desired.

When releasing the actuation portion 32 of the dome 3 within its activation, due to its resiliency or elasticity, the dome 3 re-expands into its original shape. Thereby, air and eventually also some liquid are withdrawn through the air flow channel 22 into the chamber 21. The filter 27 prevents any liquid from being forwarded into the chamber 21. Like this, reduced pressure is generated in the interior 51 of the vial 5 which is equalized by withdrawing air into the interior 51 of the vial 5 via the transfer conduit 23. The system 1 is now ready for providing a next droplet by activation of the dome 3.

In FIG. 3 a system 10 according to the invention is shown comprising a second embodiment of a device 60 according to the invention and a vial 50 with a liquid ophthalmic drug product intended to be administered dropwise into the eye of a patient. The system 10 is widely embodied identically as the system 1 of FIG. 1 and FIG. 2. In particular, the following features are identical:

The vial 50 has an interior 510, a neck 530 and a cover 520. The device 60 includes a dome 30 and a support body 20. The body 20 is equipped with a vial seat 240, a nozzle 260 and a transfer conduit 230 between the vial seat 240 and the nozzle 260. The transfer conduit 230 has an end section 2520 ending in a septum of the cover 520 and forming a portion of a spike 250. The nozzle 260 has a socket 2610 and an insert 2620 with a nozzle duct 2630 and a neck section 2640. The dome 30 has an actuation portion 320 and is connected to the body 20 by a mounting flange 280 and a corresponding mounting notch 310 such that a chamber 210 is created in the body 20.

The second system 10 of FIG. 3 is particularly different from the first system 1 of FIG. 1 and FIG. 2 in that the spike 250 and an air flow conduit 220 are differently embodied, and that no filter is provided. In more detail, the air flow conduit 220 straightly extends between the chamber 210 and the vial seat 240 wherein it projects over the transfer conduit end section 2520 to a comparably large extent. Like this, it is achieved that the air flow conduit 220 ends comparably high up in the interior 510 of the vial 50 where no drug product is arranged. Thus, an end section 2510 of the air flow conduit 220 is positioned in a portion of the interior 510 comprising air. The spike 250 is step-like embodied having a first upper piercing portion built by the air flow conduit end section 2510 and a second lower piercing portion built by the transfer conduit end section 2520.

The system 10 of FIG. 3 is identically operated as the system 1 of FIG. 1 and FIG. 2. However, when releasing the dome 30 within activation, it is assured that only air is withdrawn from the interior 510 of the vial 50 into the chamber 210 via the air flow conduit 20 since the air flow conduit end section 2510 lies high in the air containing portion of the interior 510 of the vial 50. Thus, no filter or other constructive element is required for preventing liquid to be transferred from the interior 510 of the vial 50 into the chamber 210 of the body 20.

Comparing the second system 10 of FIG. 3 to the first system 1 of FIG. 1 and

FIG. 2, it can be constructively advantageous to have a longer air flow conduit since less components, i.e. no filter, is required. In another embodiment having the longer air flow conduit, a side wall of the vial seat 240 can be extended such that the spike 250 is laterally essentially covered and protected.

However, since the sharp spike 250 of the second device 60 may involve an increased risk of injuries when inappropriately handled, the first device 6 might be preferred in some applications.

This description and the accompanying drawings that illustrate aspects and embodiments of the present invention should not be taken as limiting the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A device for providing a droplet of a liquid stored in an interior of a vial, comprising:
   a support body; and
   a resilient dome portion mounted to the support body to form a chamber comprising air, the resilient dome portion being configured to create an air flow with the air in the chamber when compressed by a user and to return to its original shape when released by the user,
   wherein the support body comprises a vial seat arranged to receive the vial, a nozzle, an air flow conduit and a transfer conduit connecting the vial seat with the nozzle,
   wherein the support body is arranged such that, when the vial is received by the vial seat,
      the air flow conduit establishes a fluid connection between the interior of the vial and the chamber,
      the transfer conduit establishes a fluid connection between the vial and the nozzle, and
      on activation of the resilient dome portion by compression by the user, the air flow delivers air into the vial such that a pressure rise is created in the interior of the vial which causes liquid to be transferred from the vial to the nozzle through the transfer conduit;

wherein, after compression and release by the user, re-expansion of the resilient dome portion causes air to be drawn through the nozzle into the interior of the vial and into the chamber;

wherein the transfer conduit includes a pointed end section dimensioned to end in or adjacent to the vial seat of the support body and is positioned to receive the liquid from the interior of the vial, when the vial is received by the vial seat; and wherein the air flow conduit includes a pointed end section that protrudes within the interior of the vial beyond the pointed end section of the transfer conduit.

2. The device of claim 1, wherein the dome portion is made of a flexible elastomeric material.

3. The device of claim 1, wherein the pointed end section of the air flow conduit comprises a puncturing member that is configured to pierce a cover of the vial to establish a flow pathway between the chamber and the interior of the vial.

4. The device of claim 1, wherein the pointed end section of the transfer conduit comprises a puncturing member that is configured to pierce a cover of the vial to establish a flow pathway between the nozzle and the interior of the vial.

5. The device of claim 4, wherein the puncturing member of the pointed end section of the transfer conduit is dimensioned to end in the cover of the vial, when the vial is received by the vial seat.

6. The device of claim 3, wherein the puncturing member of the pointed end section of the air flow conduit is dimensioned to extend into the interior of the vial, when the vial is received by the vial seat.

7. The device of claim 1, comprising an air-permeable and liquid tight filter member separating the chamber from the air flow conduit.

8. The device of claim 1, wherein the dome portion is not mounted tightly on the support body to create an air flow pathway to an exterior of the device.

9. The device of claim 1, wherein the nozzle of the support body comprises a socket and an exchangeable nozzle insert.

10. The device of claim 9, wherein the nozzle of the support body comprises a seal positioned between the socket and the nozzle insert.

11. The device of claim 1, wherein the nozzle comprises a droplet duct with an open end, the droplet duct extending between the transfer conduit and the open end, and having a droplet generation section of reduced diameter.

12. A droplet dispensing system comprising:
a device according to claim 1; and
a vial with an interior in which a liquid to be dispensed is arranged.

13. The device of claim 1, wherein the resilient dome portion and the chamber are part of a closed volume.

14. A device for providing a droplet of a liquid stored in an interior of a vial, comprising:
a support body that includes a vial seat arranged to receive the vial, a nozzle, an air flow conduit and a transfer conduit connecting the vial seat with the nozzle;
a resilient dome portion mounted to the support body to form a chamber comprising air, the resilient dome portion being configured to create an air flow with the air in the chamber when compressed by a user and to return to its original shape when released by the user; and
an air permeable and liquid tight filter member separating the chamber from the air flow conduit of the support body, wherein the filter member is arranged as a wall member between the chamber and the air flow conduit,
wherein the support body is arranged such that, when the vial is received by the vial seat,
the air flow conduit establishes a fluid connection between the interior of the vial and the chamber,
the transfer conduit establishes a fluid connection between the vial and the nozzle, and
on activation of the resilient dome portion by compression by the user, the air flow delivers air into the vial such that a pressure rise is created in the interior of the vial which causes liquid to be transferred from the vial to the nozzle through the transfer conduit; and
wherein, after compression and release by the user, re-expansion of the resilient dome portion causes air to be drawn through the nozzle into the interior of the vial and into the chamber.

15. The device of claim 14, wherein the resilient dome portion and the chamber are part of a closed volume.

16. The device of claim 14, wherein the resilient dome portion is made of a flexible elastomeric material.

17. The device of claim 14, wherein
each of the air flow conduit and the transfer conduit comprises an end section having a puncturing member,
the puncturing member of the end section of the air flow conduit is configured to pierce a cover of the vial to establish a flow pathway between the chamber and the interior of the vial,
the puncturing member of the end section of the transfer conduit is configured to pierce the cover of the vial to establish a flow pathway between the nozzle and the interior of the vial, and
the puncturing member of the air flow conduit protrudes beyond the puncturing member of the transfer conduit.

* * * * *